(12) United States Patent
McMechan et al.

(10) Patent No.: US 7,552,648 B2
(45) Date of Patent: Jun. 30, 2009

(54) MEASURING MECHANICAL PROPERTIES

(75) Inventors: David E. McMechan, Duncan, OK (US); David L. Meadows, Marlow, OK (US)

(73) Assignee: Halliburton Energy Services, Inc., Ducnan, OK (US)

(*) Notice: Subject to any disclaimer, the term of this patent is extended or adjusted under 35 U.S.C. 154(b) by 0 days.

(21) Appl. No.: 11/904,705

(22) Filed: Sep. 28, 2007

(65) Prior Publication Data

US 2009/0084189 A1 Apr. 2, 2009

(51) Int. Cl.
*G01N 3/00* (2006.01)
(52) U.S. Cl. .......................................... 73/803
(58) Field of Classification Search ............... 73/803
See application file for complete search history.

(56) References Cited

U.S. PATENT DOCUMENTS

| 4,487,056 A * | 12/1984 | Wiley ............................ 73/38 |
| 4,573,342 A | 3/1986 | Jones ............................ 73/38 |
| 5,159,828 A | 11/1992 | Steiger et al. .................. 73/38 |
| 5,325,723 A | 7/1994 | Meadows et al. ............. 73/794 |
| 5,836,200 A * | 11/1998 | Belonenko et al. .......... 73/61.79 |
| 7,380,466 B2 * | 6/2008 | Deeg ............................ 73/803 |
| 2005/0152432 A1 | 7/2005 | Hakimuddin ................ 374/53 |
| 2006/0225523 A1 | 10/2006 | Reddy et al. ............... 73/865.6 |
| 2008/0168848 A1 * | 7/2008 | Funkhouser et al. ....... 73/865.6 |

FOREIGN PATENT DOCUMENTS

| EP | 1189051 A1 | 2/2001 |
| FR | 2746920 | 10/1997 |

OTHER PUBLICATIONS

Search Report and Written Opinion for International Application No. PCT/GB2008/003240, Sep. 24, 2008.

* cited by examiner

*Primary Examiner*—Max Noori
(74) *Attorney, Agent, or Firm*—Robert A. Kent; Fish & Richardson P.C.

(57) ABSTRACT

Methods of determining the mechanical properties of a sample include applying a first pressure condition to a first portion of the sample and applying a second pressure condition to the second portion of the sample, the second pressure condition being different than the first pressure condition.

27 Claims, 6 Drawing Sheets

MEASURING MECHANICAL PROPERTIES

TECHNICAL FIELD

This disclosure relates to measuring mechanical properties.

BACKGROUND

Some well bores, for example those of some oil and gas wells, are lined with a casing. The casing stabilizes the sides of the well bore, prevents fluids (liquids or gases) in the well bore from entering the surrounding earth formations, and/or prevents fluids from zones other than the producing zones from entering the well bore.

In a cementing operation, cement is introduced down the well bore and into an annular space between the casing and the surrounding earth. The cement secures the casing in the well bore, and prevents fluids from flowing vertically in the annulus between the casing and the surrounding earth.

Different cement formulations are designed for a variety of well bore conditions, which may be above ambient temperature and pressure. In designing a cement formulation, a number of potential mixtures may be evaluated to determine their mechanical properties under various conditions.

Mechanical properties of subterranean formations in which well bores are to be formed can also affect the design of the well bores. In some instances, samples of subterranean formations are taken and subsequently evaluated to determine the mechanical properties of the formations.

SUMMARY

In one aspect, a method includes: applying a sealant to a first end of a sample and to an opposite second end of the sample while leaving a central portion of the sample substantially free of the sealant; applying a first pressure condition to a first portion of the sample; applying a second pressure condition to the second portion of the sample, the second pressure condition being different than the first pressure condition; and determining one or more mechanical properties of the sample based at least in part on the pressure conditions being applied when the sample mechanically fails.

In another aspect, a method includes: calculating a period of time required for a fluid applied to surfaces of a sample of a porous material to substantially equilibrate the pressure across the sample; applying the fluid to the sample of the porous material for at least the calculated period of time; applying a first pressure condition changed from ambient conditions to a first portion of the cylindrical sample; applying a second pressure condition changed from ambient conditions to the second portion of the cylindrical sample, the second pressure condition being different than the first pressure condition; and determining one or more mechanical properties of the cylindrical sample based at least in part on the pressure conditions present upon mechanical failure of the cylindrical sample.

Embodiments of these methods can include one or more of the following features.

In some embodiments, methods include using drilling equipment to remove the sample from a subterranean formation as a cylindrical sample. In some cases, methods include using drilling equipment to remove the cylindrical sample from a subterranean sandstone formation.

In some embodiments, methods include applying either the first pressure condition or the second pressure condition to both the first and second portions of the sample. In some cases, methods include activating an active seal to isolate a first pressure zone from a second pressure zone.

In some embodiments, the first portion of the sample includes the central portion of the sample that is substantially free of the sealant. In some cases, applying the first pressure condition comprises increasing the first pressure condition until the sample fails. In some cases, applying the second pressure condition comprises increasing the second pressure condition until the sample fails. In some cases, applying the first pressure condition comprises decreasing the first pressure condition until the sample fails. In some cases, applying the second pressure condition comprises decreasing the second pressure condition until the sample fails.

In some embodiments, methods include heating the sample before applying the sealant.

In some embodiments, methods include measuring elongation of the sample while applying the first and second pressure conditions.

In some embodiments, the first pressure condition and the second pressure condition are different than ambient conditions.

In some embodiments, the porous material has a permeability of less than one nanodarcy to in excess of 1000 darcy. The important feature being that the porous material has some permeability that will permit fluid pressure to equilibrate across a sample.

In some embodiments, methods include applying a sealant to a first end of a sample and to an opposite second end of the sample while leaving a central portion of the sample substantially free of the sealant. In some cases, the first portion of the sample includes the central portion of the sample that is substantially free of the sealant.

In some embodiments, methods include attaching a linear variable displacement transducer to the sample with a first surface of the linear variable displacement transducer oriented towards the sample and a second surface of the linear variable displacement transducer oriented away from the sample and providing a hydraulic connection between a first pressure zone acting on the first surface of the linear variable displacement transducer and a second pressure zone acting on the second surface of the linear variable displacement transducer.

Testing apparatuses and methods as described herein can be used to measure tensile strength, compressive strength, Young's modulus, Poisson's ratio, shrinkage and other properties. This versatility can reduce the number of testing devices necessary to perform comprehensive testing of a sample cement composition or of a formation sample.

In some instances, testing apparatuses and methods as described herein can be used to test samples without being unduly limited by the plasticity of the sample. For example, these testing apparatuses and methods can be applied to formation samples which are too crumbly to machine (as required by some testing methods). Moreover, only a limited amount of work is required to prepare samples for testing.

In some cases, the mechanical properties of a sample can be tested under conditions that are based on downhole conditions. For example, the tensile strength of a sample taken from a subterranean sandstone formation can be measured/estimated at pressure conditions reflecting downhole conditions. The tensile strength can be used in estimating sand production during formation and production of a well bore extending into the sandstone formation.

In some cases, the testing apparatus enables testing of samples that cannot practicably be tested in other manners. For example, the samples need not be cut, ground or trimmed, other than to cut the sample to length, or need only be minimally shaped to test their mechanical properties. In samples with a very low tensile strength or very high Young's modulus, the reduction in preparing the sample reduces the risk of unintentionally breaking or beginning a fracture such as when cutting, grinding or trimming the sample to a more complex shape. Additionally, the manner of testing (by applying a differential pressure across the sample) enables gradual deformation of weak or brittle samples that cannot be achieved with other mechanical testing methods.

The details of one or more embodiments are set forth in the accompanying drawings and the description below. Other features, objects, and advantages will be apparent from the description and drawings, and from the claims.

DESCRIPTION OF DRAWINGS

Like reference symbols in the various drawings indicate like elements.

DETAILED DESCRIPTION

The devices and methods described herein can allow an accurate measurement of mechanical properties and behaviors of samples, including cement formulations, samples taken from subterranean formations, other porous media, and other materials. The mechanical properties that can be measured include, for example, tensile strength, compressive strength, shrinkage, and other properties. For example, a sample cement composition can be cured or partially cured at downhole conditions (e.g., temperatures and/or pressures elevated above ambient conditions) before differential pressures are applied to discrete portions of the cement sample (e.g., a first pressure is applied to one section of the cement sample and a second pressure that is different than the first pressure is applied to another section of the cement sample). Mechanical properties of the cement sample can be calculated based on the response of the sample to the differential pressures. In another example, differential pressures can be applied to a sample (e.g., a core sample) taken from a subterranean formation. Mechanical properties of the subterranean formation can be determined based on the response of the sample to the differential pressures.

As used herein, "cement" and "cement composition" encompass a fluid mixture that hardens into solid, and may be any agent suitable to bond casing or other tubulars to well bore walls or to other tubing used for downhole applications. Some examples of cement include hydraulic cement (e.g., Portland cement formulations) and non-hydraulic cement (e.g., polymer resin formulations). As used herein, "curing" refers to the reactions through which cement hardens from a fluid mixture into a solid. In some instances, the devices and methods discussed herein can be used to measure mechanical properties at temperatures and pressures that simulate downhole conditions.

Figure 1:
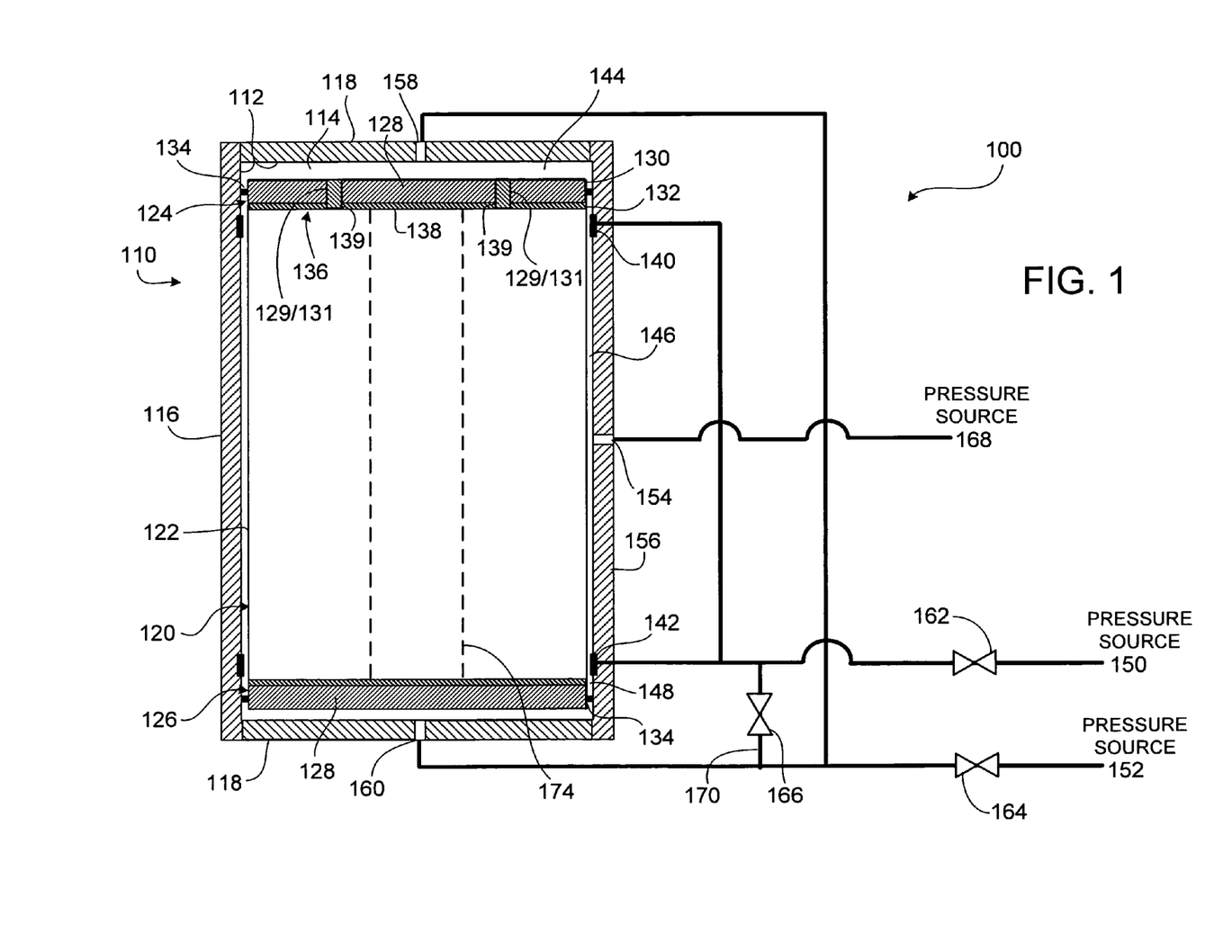
FIG. 1 is a schematic view of an embodiment of a testing apparatus.

Referring to FIG. 1, an example testing apparatus 100 includes a pressure vessel 110 having inner surfaces 112 defining an interior cavity 114. In some instances, pressure vessel 110 includes a hollow cylindrical body 116 and end caps 118. The end caps 118 are attached to the cylindrical body 116 to form a pressure tight seal. For example, the end caps 118 can be threaded or otherwise fastened to the cylindrical body 116. A seal or seals (e.g., o-rings) can be provided to enhance the pressure-tight fit between the cylindrical body 116 and the end caps 118. In some cases, the cylindrical body 116 and end caps 118 are made of steel or other suitable materials. In some embodiments, the pressure vessel 110 can be configured with other shapes (e.g., non-cylindrical or shaped similar or the same as the shape of the as-collected sample).

A sample container 120 is disposed in the interior cavity 114 of the pressure vessel 110. Sample container 120 has portions including (e.g., formed of) metallic, plastic, or other suitable material operable to communicate changes of pressure to a sample in the sample container 120. For example, the sample container 120 can include a first piston 124, a second piston 126 spaced apart from the first piston 124; and a sample sleeve or sidewalls 122 extending between the first piston 124 and the second piston 126. Sidewalls 122 and pistons 124 or 126 can be formed of metallic, plastic, or other suitable material operable to communicate changes of pressure to a sample in the sample container 120.

The pistons 124, 126 can include in some embodiments a plate 128 having an outer surface 130 that is configured to match a corresponding portion 132 of the inner surfaces 112 of the pressure vessel 110. Plates can be sized and configured such that the outer surface 130 of each plate 128 has a first perimeter that is smaller than a second perimeter of the corresponding inner surface 132 of the pressure vessel 110 (e.g., the plate 128 fits within the pressure vessel 110). Upper plate 128 can include two fill holes 129 that can be sealed with associated plugs 131. Plates 128 can include (e.g., are made of) steel or other suitable materials.

In some embodiments, sidewalls 122 are formed of metallic, plastic, or other suitable material(s) (e.g., rubber, filter paper, brass, or aluminum) operable to communicate changes of pressure to a sample in the sample container 120. In addition, the material used for the sidewalls 122 is capable of containing a slurry, including a cement slurry. For example, a material transmissive to water and capable of containing a slurry can be used to form the sidewalls 122. In some cases, the sidewalls 122 include a micro-porous material. As used herein, micro-porous materials are materials whose internal structure contains sufficient interconnected void spaces to allow for the transmission of fluids such as water or nitrogen gas through the material. For example, filter paper would be considered a micro-porous material. In some cases, sidewalls 122 include a macro-porous material. As used herein, macro-porous materials are materials in which discrete bores extend directly through the material from one side of the material to an opposite side of the material. Macro-porous materials may also have micro-porous characteristics (e.g., filter paper that has been needled to form discrete holes extending through the filter paper) or may have an internal structure substantially impervious to fluids (e.g., a perforated Kapton® film). By attaching sidewalls 122 to circular pistons 124, 126, cylindrical sample container 120 can be formed.

The sample container 120 can have sufficient structural stability to hold a cement slurry in a desired shape while it cures. For example, a thin rubber sleeve can be stiffened with closely spaced o-rings or a thin rubber sleeve can be stiffened with an o-ring glued on the outside of the sleeve in a spiral pattern or a thicker rubber sleeve can be used.

In some instances, spacers can be installed between the plates 128 and the pressure vessel 110 to maintain the relative spacing position between the plates 128 and the interior surfaces of the pressure vessel 110. For example, the pistons 124, 126 can include a spacer member 134 disposed between the outer surface 130 of the plate and the corresponding inner surface 132 of the pressure vessel 110. Spacer members 134 help maintain a desired position of the sample container 120 relative to the inner surfaces 112 of the pressure vessel 110. Spacer members 134 can be o-rings arranged to provide a small but discrete distance (e.g., 0.001 inch, 0.005 inch, or 0.01 inch) between the sample sleeve 122 and interior surface 132 of the body 116 of the pressure vessel 110.

Some testing apparatuses include low friction inserts located adjacent to the plates to limit bonding between the pistons and the composition being tested. For example, testing apparatus 100 includes inserts 136 disposed inside the sample container 120 adjacent each plate 128. The inserts 136 include (e.g., are made of and/or are layered with) a material having a low coefficient of friction (e.g., less than about 0.2, 0.1, 0.05, or 0.025). In some embodiments, inserts 136 can be thin stainless steel plates coated with Teflon® or other suitable materials. This provides inserts 136 with a surface 138 having a first friction coefficient that is lower than a second friction coefficient of the plates. Top insert 136 includes two fill holes 139 whose locations match the locations of the fill holes extending through the top plate 128.

In order to enable application of differential pressures to a sample being tested, some testing apparatuses can also include seals dividing the interior cavity into multiple pressure-tight sections. As the seals are used during testing, the seals are configured to cooperate with the sample container and sample in forming the multiple pressure-tight sections. For example, seals extending between interior walls of a pressure vessel to engage a sample container and sample can form multiple pressure-tight sections that would be in fluid communication in the absence of the sample container and sample. The seals can be active seals (e.g., seals that are pressurized to switch from an inactive first configuration to an active second configuration with a smaller inner diameter) that are activated or can be passive seals. For example, the active seals can be activated after a sample cement composition is at least partially cured. Thus, the term dividing is used broadly to indicate seals disposed at the interface between discrete sections of a pressure vessel whether or not the seals limit fluid communication between the sections of the pressure vessel in all configurations and/or in the absence of a sample container and sample.

For example, referring again to FIG. 1, testing apparatus 100 includes a first seal member 140 and a second seal member 142 that are disposed adjacent to inner surfaces 112 of pressure vessel 110 such that the seal members 140, 142 are between the inner surfaces of the pressure vessel 110 and the sample container 120 when the sample container is placed in pressure vessel 110 for testing a sample. The first seal member 140 divides a first section 144 of the interior cavity 114 from a second section 146 of the interior cavity 114 and the second seal member 142 divides a third section 148 of the interior cavity 114 from the second section 146 of the interior cavity 114 such that the second section 146 of the interior cavity 114 is located between the first and third sections 144, 148 of the interior cavity 114.

In some embodiments, including the illustrated embodiment, the first and second seals 140, 142 are active seals which are switchable between a first configuration (shown in FIG. 1) in which the active seal is spaced apart from the sample container 120 and a second configuration (not shown) in which the active seals engage the sample container 120. Thus, when the seals 140, 142 are in their first configuration, the first, second, and third sections 144, 146, 148 of the interior cavity are in fluid communication with each other. When sample container 120 containing a sample is inserted and seals 140, 142 are activated to engage the sample container 120 and sample, the first, second, and third sections 144, 146, 148 of the interior cavity 114 can be isolated from each other such that differential pressures can be applied to individual sections as described in more detail below. Pressure applied by first pressure source 150 can activate seals 140, 142. In this embodiment, spacer members 134 have apertures extending therethrough which provide fluid communication between opposite sides of the spacer members 134.

Testing apparatuses can also include ports extending through the pressure vessel into the multiple sections of their interior cavities. For example, referring again to FIG. 1, testing apparatus 100 includes a central port 154 extending from an outer surface 156 of the pressure vessel 110 to the second section 146 of the interior cavity 114 of the pressure vessel 110. Testing apparatus 100 also includes a first port 158 extending from an outer surface 156 of the pressure vessel 110 to the first section 144 of the interior cavity 114 of the pressure vessel 110 and a third port 160 extending from the outer surface of the pressure vessel 110 to the third section 148 of the interior cavity 114 of the pressure vessel 110.

First and second pressure sources 150, 152 and associated piping are used to independently control pressure conditions in the multiple sections 144, 146, 148 of the interior cavity 114 of the pressure vessel 110. First valve 162 and second valve 164 are interposed between first pressure source 150 and second pressure source 152, respectively, and the remainder of the associated piping system. Isolation valve 166 is disposed on interconnect piping 170 that can provide fluid communication between the portions of the piping connected to first and second ports 158, 160. Pressure source 168 is connected to central port 154. Pressure source 150 allows engagement of the active seals 140, 142 before opening flow to the second section 146 of the cell. Other arrangements of valves and piping can also be used to apply differential pressures to discrete sections of the interior cavity 114 of the pressure vessel 110. The pressure control can be effected with various systems such as by using pressurized gas cylinders, pumps or the like.

Testing apparatuses can include sensors to measure parameters used to calculate properties of samples being tested. For example, testing apparatus 100 may include one or more linear variable displacement transducers (LVDTs) positioned at various intervals, such as at 120 degree intervals around a circle if three were used, between upper steel plate 128 and end cap 118 or in other suitable positions such as a single transducer in the center or some other location. The average reading of the LVDTs can be used to characterize the length change of the sample during testing. Sensors also could be positioned around the perimeter of testing apparatus 100. Other sensors, such as strain gauges, can be used in addition to or in place of the LVDTs to measure relevant parameters. For example, four strain gauges (two vertical and two tangential) could be attached to interior surfaces of a rubber sleeve to provide material data that would be difficult to obtain otherwise. Alternatively, strain gauges could be attached to exterior surfaces of an aluminum sleeve. Similarly, the amount of fluid (e.g., water, hydrocarbon or gas) pumped into the pressure vessel 110 as the cement cures can provide a measure of cement shrinkage. Pressure sensors can be included to measure pressures present during testing.

Temperature can be controlled to simulate downhole conditions during testing or at other times. For example, in testing cement, the testing apparatus 100 and cement slurry can be preheated during mixing. The desired temperature can be maintained as the sample cement composition cures using external heating elements (e.g., heater coils or stainless steel heater bands) or placing the testing apparatus 100 in an oven.

Figure 2:
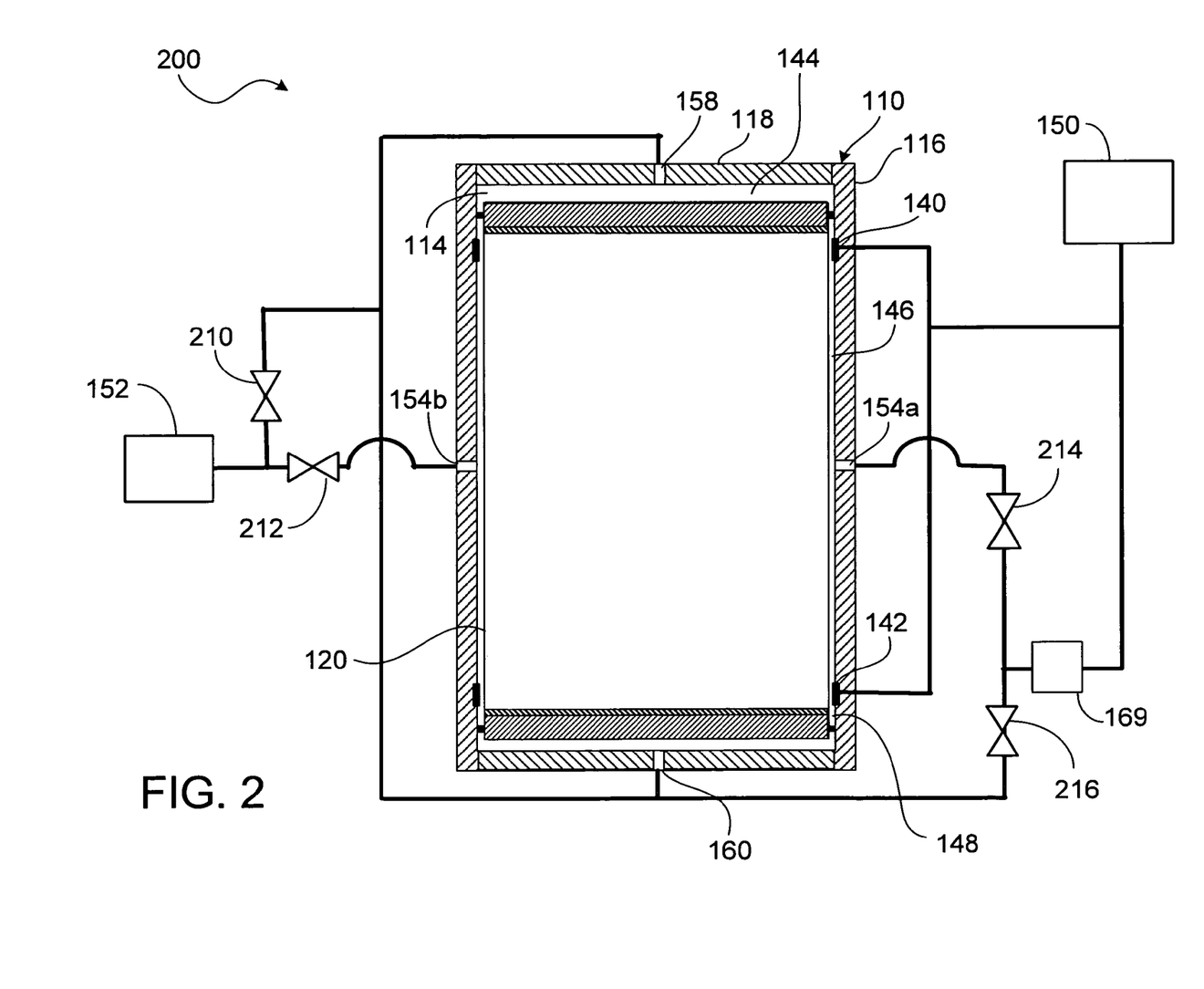
FIG. 2 is a schematic view of another embodiment of a testing apparatus.

Referring to FIG. 2, another example testing apparatus 200 is configured to enable a single testing apparatus to be used to perform both compressive and tensile strength tests. Testing apparatus 200 is substantially similar to testing apparatus 100 but includes an alternate arrangement of pressure sources, valves, and piping to apply differential pressures to discrete sections of the interior cavity 114 of the pressure vessel 110.

Testing apparatus 200 includes a pressure vessel 110 with a hollow body 116 and end caps 118. The end caps 118 are attached to the body 116 to form a pressure tight seal. The sample container 120 is disposed in the pressure vessel 110. Active seals 140, 142 can isolate the first, second, and third sections 144, 146, 148 of interior cavity 114 from each other when sample container 120 is present. First port 158, central ports 154a, 154b, and third port 160 extend through the pressure vessel 110 to the interior cavity 114 of the pressure vessel 110.

First and second pressure sources 150, 152 and associated piping are used to independently control pressure conditions in the multiple sections 144, 146, 148 of the interior cavity 114 of the pressure vessel 110. A pressure relief valve 169 is disposed on the piping connected to central port 154a and allows engagement of the active seals 140, 142 before opening flow to the interior cavity 114 of the cell. Flow paths from the first and second pressure sources 150, 152 can each be connected various combinations of the ports 154, 158, 160 based on the settings of valves 210, 212, 214, 216 as required for a particular test.

For example, when performing a tensile strength test, valve 210 and valve 214 can be opened and valve 212 and valve 216 can be closed. After a sample is placed in sample container 120, pressure source 152 can be used to set the pressure in the pressure vessel 110 at which the sample will be cured by supplying pressurizing fluid to the first port 158 and the third port 160. At this point, the active seals 140, 142 are in their inactive state. After curing to the extent desired, the pressure source 150 can be operated to supply pressurizing fluid to the active seals 140, 142 and, since valve 214 is open and valve 216 is closed, to the central port 154a. Applying pressure to the active seals 140, 142 activates them to isolate first, second, and third sections 144, 146, 148 of the interior cavity 114 from each other. Pressure source 150 can be used to apply increasing pressure to the second section 146 via port 154a until the sample fails.

In another example, when performing a compressive strength test, valve 210 and valve 214 can be closed and valve 212 and valve 216 can be opened. After a sample is placed in sample container 120, pump 152 can be used to set the pressure in the pressure vessel 110 at which the sample will be cured by supplying pressurizing fluid to the central port 154b. At this point, the active seals 140, 142 are in their inactive state. After curing to the extent desired, the pump 150 can be operated to supply pressurizing fluid to the active seals 140, 142 and, since valve 214 is closed and valve 216 is opened, to the first port 158 and the third port 160. Applying pressure to the active seals 140, 142 activates them to isolate first, second, and third sections 144, 146, 148 of the interior cavity 114 from each other. Pump 150 can be used to apply increasing pressure to the first and third section 144, 148 via the first and third ports 158, 160 until the sample fails.

Methods of determining properties of a sample can be performed using testing apparatuses to apply differential pressures on different portions of a sample. In testing cement, a sample container can be placed in the interior cavity of a pressure vessel before the sample container is filled with a sample cement composition to be tested. The sample cement composition can be cured or partially cured inside the pressure vessel at temperatures and/or pressures that simulate downhole conditions. Seals can separate multiple sections of the interior cavity of the pressure vessel from each other. A first pressure can be applied in one section and a different pressure can be applied in another section. Differential pressures can be applied to different portions of the sample being tested until the sample fails. Mechanical properties of the sample can be calculated based, at least in part, on conditions and properties associated with the pressure vessel and the sample as the differential pressure is applied.

Figure 3:
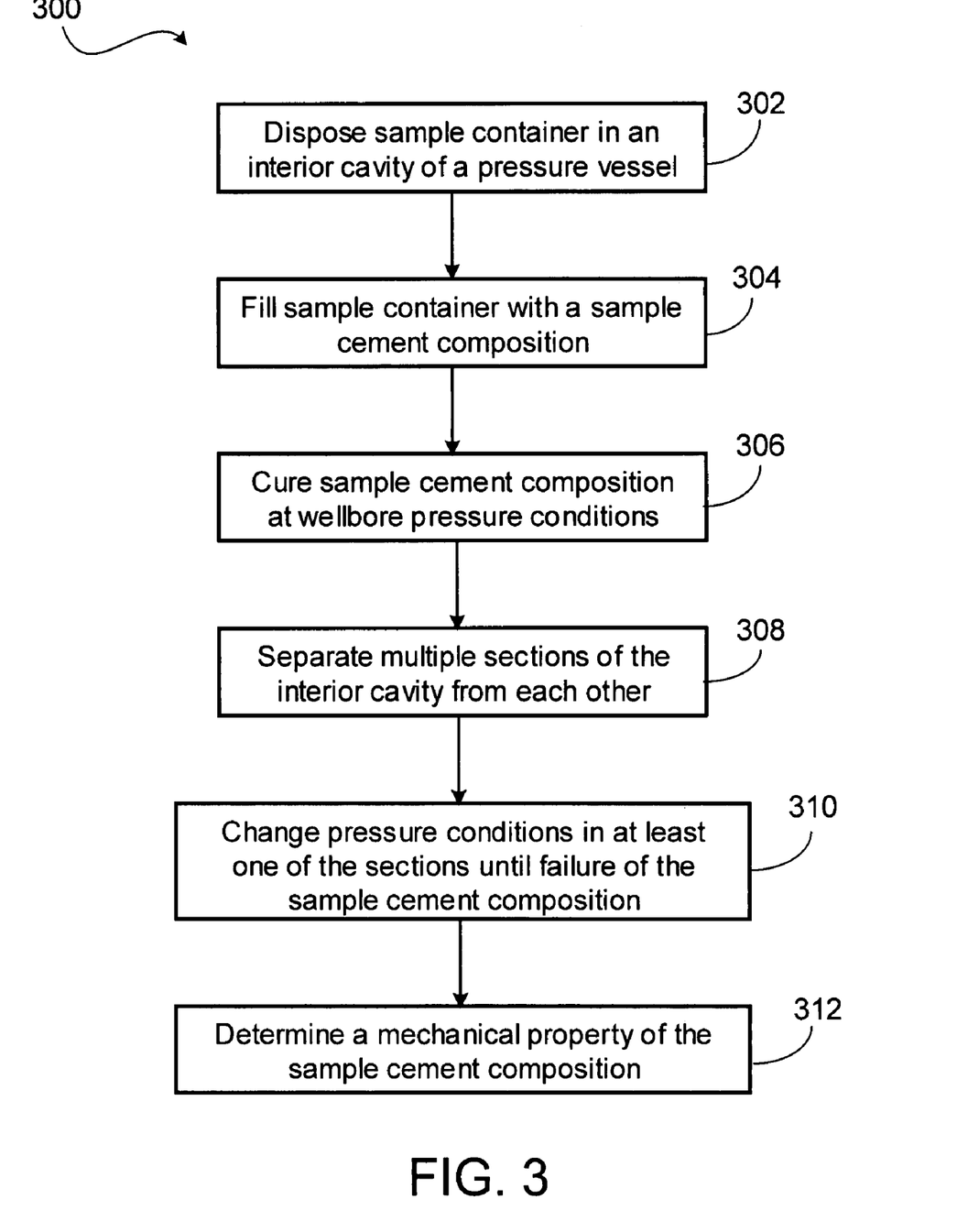
FIG. 3 is a flowchart of an embodiment of testing method.

Referring to FIG. 3, an example method 300 is described for testing cement. However, the method 300 can be applied to testing other materials. The example method 300 can include disposing a sample container 120 in an interior cavity 114 of a pressure vessel (operation 302). For example, a rubber sleeve can be glued to two circular steel plates (one at the top of the rubber sleeve and the other at the bottom of the rubber sleeve) to form a cylindrical sample container. The top steel plate can have multiple holes extending therethrough to be used in filling the sample container. For example, the top steel plate can have two holes spaced apart from each other along a single diameter of the top steel plate at equal distances from the center of the plate. In some cases, there may be more than two holes and/or the locations of the holes may be varied (e.g., the top steel plate may be tapered, getting thinner toward the center where it has a hole, with the second hole somewhere else on the plate).

The sample container can be filled with a sample cement composition (operation 304). For example, a cement slurry can be added to (e.g., pumped into or poured into) the sample container through a first hole while air and water escape from the sample container through a second hole. When slurry escapes through the second hole, the entire sample container is filled with slurry. Other ways of filling the sample container are also possible (e.g., using a syringe to fill a sample container from the bottom to the top). After the sample container is filled with slurry, the holes can be plugged. The sample container can be filled and then placed in the pressure vessel or the sample container can be placed in the pressure vessel and then filled.

The sample cement composition can be cured within the interior cavity of the pressure vessel at specified pressures and temperatures (operation 306). The specified pressures and temperatures can be chosen to simulate well bore pressure and/or temperature conditions or other pressure and/or temperature conditions under which a cement sample's properties are of interest. Simulated downhole pressure and temperature conditions can be actual downhole conditions (e.g., 350 degrees Fahrenheit and 15,000 psi) or modified conditions. The pressure vessel can be heated using a thermal blanket or through the application and/or circulation of a heated fluid (e.g., water) to interior portions of the pressure vessel, with the temperature being controlled by internal thermocouples. A pressurizing fluid (e.g., water or a gas such as nitrogen) can be pumped into the pressure vessel through ports extending through the walls of the pressure vessel. Water is inexpensive, can be safer to use than pressurized gases, and simplifies associated logistics. By controlling the temperature and/or pressure present while the sample cement composition cures, the properties of the sample cement composition measured during testing closely reflect the properties of similar cement compositions during actual use.

Seals can be used to separate sections of the interior cavity from each other (operation 308). For example, a first seal member disposed between an inner surface of the pressure vessel and the sample container can separate a first section of the interior cavity from a second section of the interior cavity and a second seal member disposed between the inner surface of the pressure vessel and the sample container can separate a third section of the interior cavity from the second section of the interior cavity such that the second section of the interior cavity is located between the first and third sections of the interior cavity.

In some cases, the seals are active seals and using the first seal member and using the second seal member can include activating the active seals to engage the sample container after the sample cement composition has at least partially cured. Pressure can be applied to activate the seals independently of the application of differential pressure to the separate section. Alternatively, pressure can be applied to activate the seals in conjunction with the application of the differential pressures (e.g., conduits in fluid communication with each can be used to supply pressurizing fluid to both the second section of the interior cavity and to active seals that separate the second section from the first and third sections). By using active seals, the sample cement composition can be allowed to cure before the seals engage the sample container in the sample cement composition contained within. This can avoid indentations in the sample cement composition that can result if seals engage sample cement composition before it cures. It is advantageous to avoid such indentations because they can be an anomalous point of weakness in the sample whose early failure can distort the calculation of the properties being measured.

After the sections of the interior cavity are separated from each other, pressure conditions in at least one of the sections can be changed to induce failure of the cured sample cement composition (operation 310). For example, pressure conditions can be changed in at least one of the first, second, and third sections of the pressure vessel until the failure of the cured sample cement composition. In some cases, changing pressure conditions comprises increasing pressure conditions in the second section of the interior cavity (e.g., by pumping water into the second section of the interior cavity through a central port extending from an outer surface of the pressure vessel to the second section of the interior cavity of the pressure vessel). In some cases, changing pressure conditions comprises increasing pressure conditions in the first and third sections of the interior cavity of the pressure vessel (e.g., by pumping water into the first and third sections of the interior cavity through a first port extending from an outer surface of the pressure vessel into the first section the interior cavity of the pressure vessel and through a third port extending from an outer surface of the pressure vessel to the third section of the interior cavity of the pressure vessel). Failure of the cement sample can be indicated, for example, by a rapid change in LVDT readings, by a large increase in water needed to maintain pressure in a section of the pressure vessel, and/or by water being expelled from another section of the pressure vessel.

Based at least in part on pressure conditions in at least one of the first, second, and third sections of the pressure vessel, one or more mechanical properties of the sample cement composition can be determined (operation 312).

The tensile strength of a sample cement composition can be determined (e.g., precisely determined or estimated) by applying increasing levels of fluid pressure to a central portion of a cylindrical cement sample while the end of portions of the cylindrical cement sample remain in a baseline pressure (e.g., atmospheric pressure or pressure consistent with downhole conditions). The fluid pressure at failure may be equal or proportional to the tensile strength of the cement composition. During such testing, the sample cement composition's change in length can be measured (e.g., using LVDTs) to provide a basis for calculating Young's modulus using standard methods. In some embodiments, cement shrinkage during curing can be measured by recording the volume of water pumped into the testing apparatus to maintain a constant pressure during curing.

A sample cement composition can also be tested under compression. For example, pressures can be increased in the first and third sections of a three-section testing apparatus until failure of the sample cement specimen. To perform compression testing, the cement testing apparatus can be configured with sufficient space between the exterior walls of the sample container and the interior walls of the pressure vessel to allow for the cement composition being tested to expand laterally due to Poission's ratio effect. For example, a 2 inch by 4 inch cement specimen with a Young's modulus of 3000 ksi and a Poisson's ratio of 0.2 should fail at a vertical strain of about 0.002 and a horizontal strain of about 0.0004. At this point, the specimen's radius should have increased by about 0.0004 inch and at least this much gap must be provided between the sample container and the pressure vessel.

Using this method, multiple tests can be conducted in parallel using a single set of pressure source. For example, the pressure source can be used to pressurize multiple pressure vessels with each pressure vessel sealed and set aside for the cement to cure while other pressure vessels are being filled or tested. After the various cement specimens have reached the desired stage of curing, they can be tested to failure one at a time with the pressure source.

Figure 4:
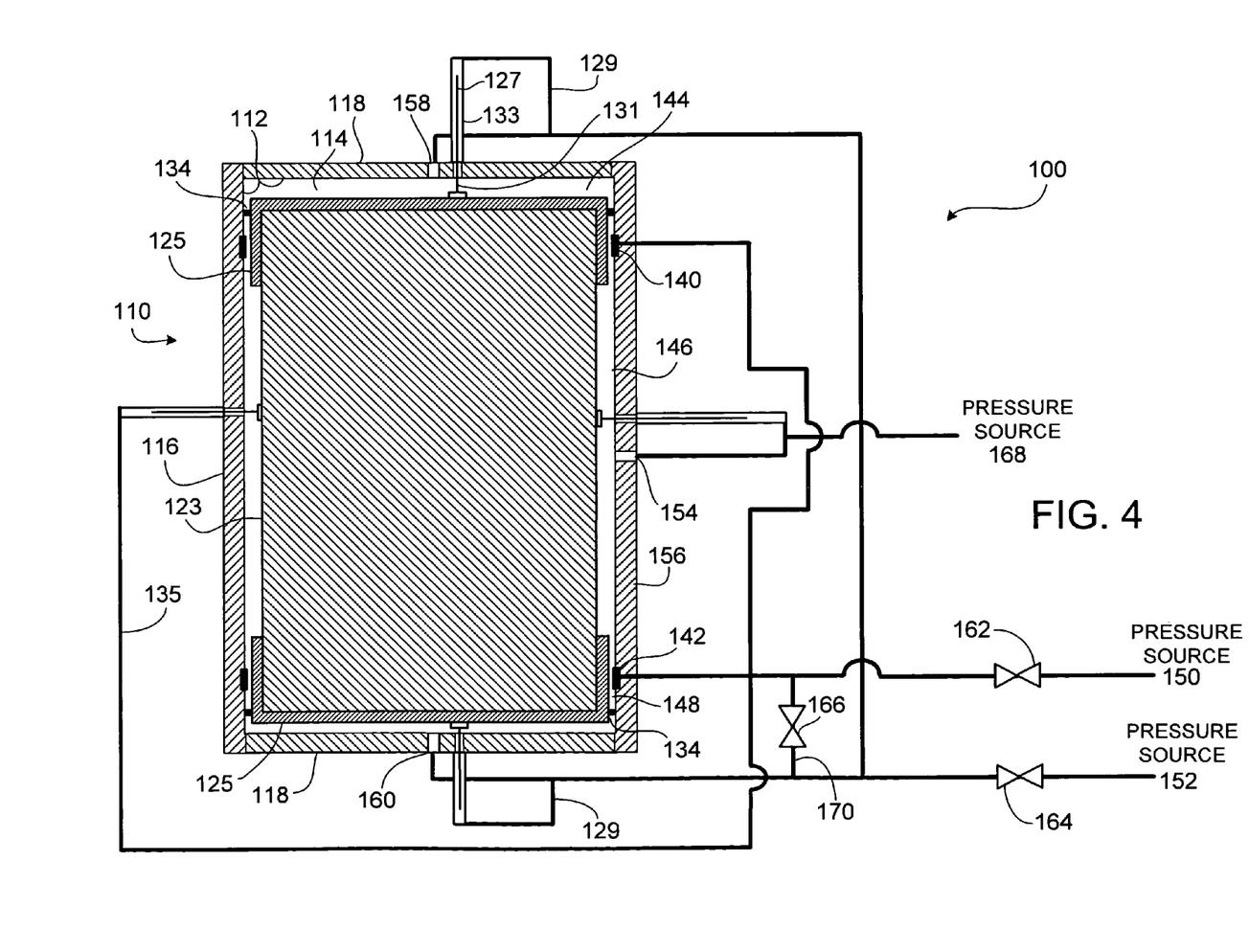
FIG. 4 is a schematic view of another embodiment of a testing apparatus.

Referring to FIG. 4, testing apparatus 100 can be configured to test a sample 123 that is solid prior to insertion into the testing apparatus 100 (e.g., a core sample taken from a subterranean formation, cured cement or other material). As described above with reference to FIG. 1, testing apparatus 100 includes pressure vessel 110 having inner surfaces 112 defining an interior cavity 114. In some instances, pressure vessel 110 includes a hollow cylindrical body 116 and end caps 118 attached to the cylindrical body 116 to form a pressure tight seal. In some embodiments, the pressure vessel 110 can be configured with other (e.g., non-cylindrical) shapes and with or without end caps 118.

Sample 123 is disposed in the interior cavity 114 of the pressure vessel 110. In some instances, a sealant 125 coats the upper and lower ends of sample 123. The sealant 125 coats the surface and isolates or substantially isolates the first, second, and third sections 144, 146, 148 from each other. In some instances, it extends a discrete distance into the pores of the sample. It may be desirable to use the sealant 125 when sample 123 is too fluid permeable to practicably test. For example, it may be desirable to use the sealant 125 when the sample is so permeable that that the fluid pressure differential used to test the mechanical properties cannot be or cannot practicably be maintained during the test. In certain instances, the sealant 125 can be used when testing a sample comprising sandstone. The sealant 125 can also be omitted. For example, it may be desirable to omit the sealant 125 when the sample is relatively impermeable.

In some instances, spacers can be installed between the sample 123 and the pressure vessel 110 to maintain the relative spacing position between sample 123 and the interior surfaces of the pressure vessel 110. For example, in one embodiment, spacer members 134 are disposed between the outer surface of sample 123 and the corresponding inner surface 132 of the pressure vessel 110. Spacer members 134 help maintain a desired position of the sample 123 relative to the inner surfaces 112 of the pressure vessel 110. Spacer members 134 can be o-rings arranged to provide a small but discrete distance (e.g., 0.001 inch, 0.005 inch, or 0.01 inch) between the sample 123 and interior surface 132 of the body 116 of the pressure vessel 110. In certain instances, the spacing between the sample 123 and the inner surface 132 of the pressure vessel 110 is selected to allow deformation of the sample during testing without the sample 123 impacting the pressure vessel 110.

For example, referring again to FIG. 4, testing apparatus 100 includes a first seal member 140 and a second seal member 142 that are disposed adjacent to inner surfaces 112 of pressure vessel 110 such that the seal members 140, 142 are between the inner surfaces of the pressure vessel 110 and the sample container 120 when the sample container is placed in pressure vessel 110 for testing a sample cement composition. The first seal member 140 and sealant 125 divide a first section 144 of the interior cavity 114 from a second section 146 of the interior cavity 114 and the second seal member 142 and sealant 125 divide a third section 148 of the interior cavity 114 from the second section 146 of the interior cavity 114 such that the second section 146 of the interior cavity 114 is located between the first and third sections 144, 148 of the interior cavity 114.

Testing apparatuses can also include ports extending through the pressure vessel into the multiple sections of their interior cavities. For example, testing apparatus 100 includes a central port 154 extending from an outer surface 156 of the pressure vessel 110 to the second section 146 of the interior cavity 114 of the pressure vessel 110. Testing apparatus 100 also includes a first port 158 extending from an outer surface 156 of the pressure vessel 110 to the first section 144 of the interior cavity 114 of the pressure vessel 110 and a third port 160 extending from the outer surface of the pressure vessel 110 to the third section 148 of the interior cavity 114 of the pressure vessel 110.

First and second pressure sources 150, 152 and associated piping are used to independently control pressure conditions in the multiple sections 144, 146, 148 of the interior cavity 114 of the pressure vessel 110. First valve 162 and second valve 164 are interposed between first pump 150 and second pump 152, respectively, and the remainder of the associated piping system. Isolation valve 166 is disposed on interconnect piping 170 that can provide fluid communication between the portions of the piping connected to central port 154 and the portions of the piping connected to first and second ports 158, 160. Pressure source 168 is connected to central port 154. Other arrangements of pumps, valves, and piping can also be used to apply differential pressures to discrete sections of the interior cavity 114 of the pressure vessel 110. The pressure control systems can be provided by one or more pressurized gas cylinders, fluid pumps or the like.

Testing apparatuses (in any of the above configurations) can include sensors to measure parameters used to calculate properties of samples being tested. For example, testing apparatus 100 may include one or more linear variable displacement transducers (LVDTs) 127 positioned about the sample. In certain embodiments, the LVDT has a measurement pin 131 whose relative movement inside of a housing 133 is measured to determine displacement of the sample 123. For example, the LVDTs 127 can be positioned at the axial ends of the sample 123 and/or around the circumferential surfaces of the sample 123. In certain instances, when multiple transducers are used, the LVDTs 127 can be positioned at 120 degree intervals around a circle on the top end of the sample 123 or in other suitable positions. The average reading of the LVDTs can be used to characterize the length change of the sample during testing. Similar configurations of LVDTs can be used on the circumferential surfaces of the sample 123. Other sensors, such as strain gauges, can be used in addition to or in place of the LVDTs to measure relevant parameters. For example, four strain gauges (two vertical and two tangential) could be attached to sample 123. Pressure sensors can be included to measure pressures present during testing.

The LVDTs 127 can be adhesively attached to the sample 123 by the sealant 125 and/or by a separate adhesive. In instances where the sample is cured, for example cured in the testing apparatus, the tips of the LVDTs' pins 131 can be cured into the sample. In some cases, the LVDTs 127 can include a passage 129 extending from the various pressure supply lines to the back of the LVDTs 127 to provide hydraulic communication between the pressure supplied to the sections 144, 146, 158 of the testing apparatus 100 and LVDTs 127. Such pressure communication equalizes or substantially equalizes the pressure across the LVDTs 127 to hydraulically balance the forces applied to both sides of the LVDTs' pins 131. Such hydraulic balance reduces or eliminates the tendency of the pin 131 to move out of the cavity 114 and away from the sample 123 due to pressure in the cavity 114. In some embodiments, other mechanisms (e.g., spring loading) are used to cause the LVDTs 127 to stay in contact with the sample 123.

Figure 5:
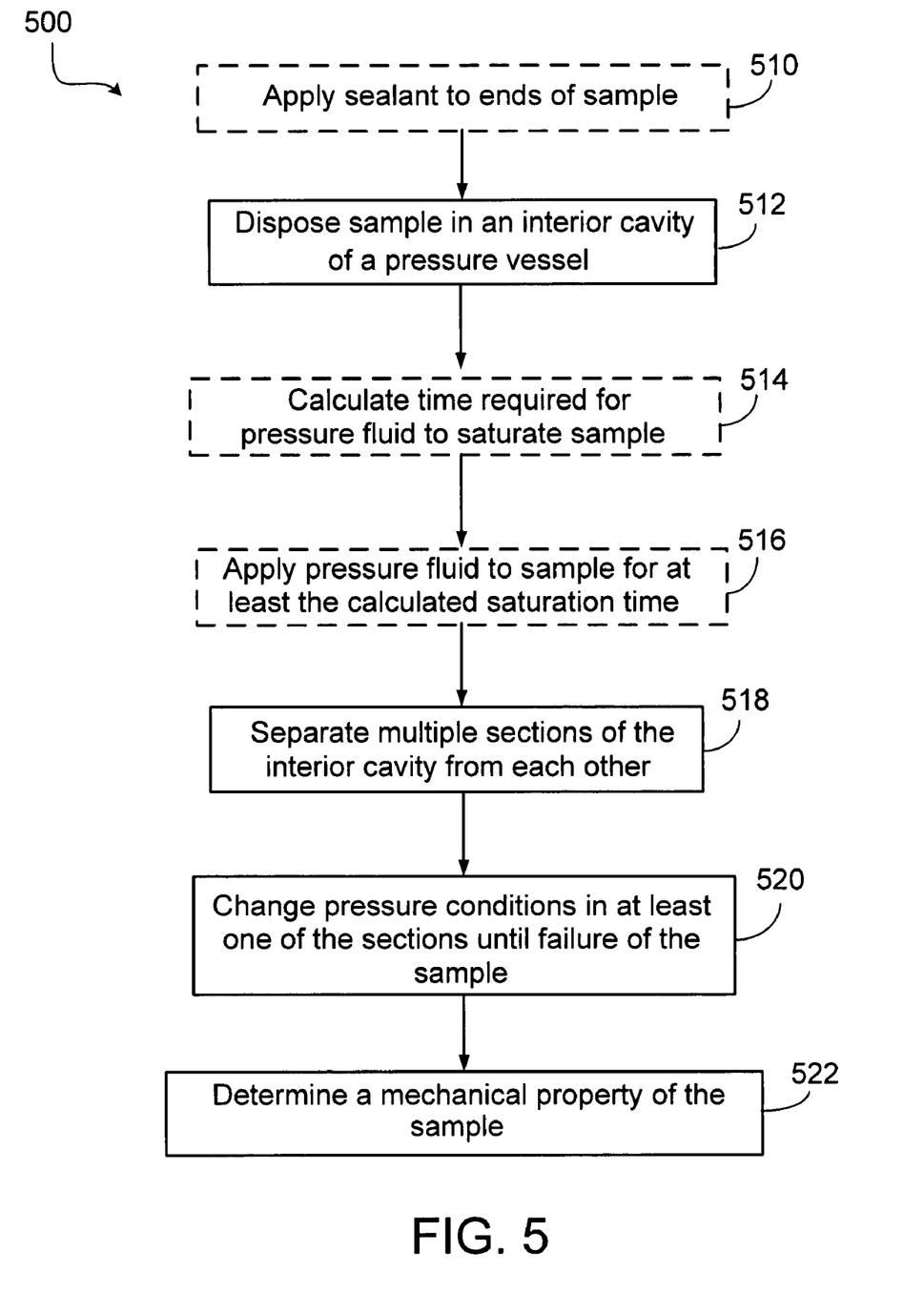
FIG. 5 is a flowchart of an embodiment of testing method.

Referring to FIG. 5, an example method 500 can include preparing a sample for testing. In some cases, the sample is a core sample obtained by using drilling techniques to obtain a core sample from a subterranean zone such as, for example, a sandstone formation. If a core sample, the testing apparatus 100 can be sized to receive the core sample without further cutting, grinding or trimming of the core sample, other than to cut the sample to length. This is particularly useful when the sample is crumbly, and could not withstand substantial cutting, grinding or trimming such as needed to make dog bone, necked or other non-cylindrically shaped samples. In some instances, preparing the sample can include applying a sealant to the ends of the sample (operation 510). Suitable sealants can include resins and any other material which will provide a substantial reduction in the permeability of the sample. The term "resin" as used herein refers to any of numerous physically similar polymerized synthetics or chemically modified natural resins including thermoplastic materials and thermosetting materials. Resins suitable for use in the present invention include all resins known and used in the art. One type of resin coating material suitable for use in the compositions and methods of the present invention is a two-component epoxy based resin comprising a liquid hardenable resin component and a liquid hardening agent component. Examples of hardenable resins that can be used in the liquid hardenable resin component include, but are not limited to, organic resins such as bisphenol A diglycidyl ether resin, butoxymethyl butyl glycidyl ether resin, bisphenol A-epichlorohydrin resin, bisphenol F resin, polyepoxide resin, novolak resin, polyester resin, phenol-aldehyde resin such as phenol formaldehyde resins, urea-aldehyde resin, furan resin, urethane resin such as polyurethane resins and hybrids and copolymers thereof, a glycidyl ether resin, other similar epoxide resins and combinations thereof. Additional resins include, but are not limited to phenolic resins, furan/furfuryl alcohol resins, phenolic/latex resins, polyester resins and hybrids and copolymers thereof, acrylate resins, and mixtures thereof. In some cases, the sealant and/or sample can be heated to increase the likelihood that the sealant will enter to pores of the sample enough to achieve a good seal. After sample preparation is complete, the sample can be disposed in an interior cavity of a pressure vessel (operation 512).

In some cases, the time required for the pressurizing fluid to substantially saturate the sample is then calculated (operation 514). Factors including the permeability of the sample, characteristics of the specific fluid being used (e.g., viscosity), the dimensions of the sample, and the initial pressure being applied affect the time required. The pressurizing fluid can be pumped into the pressure vessel through ports extending through the walls of the pressure vessel. The pressurizing fluid can be applied to the entire sample at the desired initial pressure for at least the calculated saturation (operation 516).

Seals can be used to separate sections of the interior cavity from each other (operation 518). For example, a first seal member disposed between an inner surface of the pressure vessel and the sample can separate a first section of the interior cavity from a second section of the interior cavity and a second seal member disposed between the inner surface of the pressure vessel and the sample can separate a third section of the interior cavity from the second section of the interior cavity such that the second section of the interior cavity is located between the first and third sections of the interior cavity. For porous samples, the seal members can cooperate with the sealant applied to ends of the sample to separate sections of the interior cavity from each other.

In some cases, the seals are active seals and using the first seal member and using the second seal member can include activating the active seals to engage the sample. Pressure can be applied to activate the seals independently of the application of differential pressure to the separate sections. Alternatively, pressure can be applied to activate the seals in conjunction with the application of the differential pressures (e.g., conduits in fluid communication with each can be used to supply pressurizing fluid to both the second section of the interior cavity and to active seals that separate the second section from the first and third sections). By using active seals, the sample can be saturated with the pressurizing fluid, which may comprise for example a gas, water or hydrocarbon, before the seals engage the sample and differential pressures are applied. In some instances, this saturation of the sample with the pressurizing fluid can reduce the likelihood of inaccurate measurements (resulting in inaccurate determinations of mechanical properties of the sample) due to variations of pressure present at different depths from surfaces of the sample.

After the sections of the interior cavity are separated from each other, pressure conditions in at least one of the sections can be changed to induce failure of the sample (operation 520). For example, pressure conditions can be changed in at least one of the first, second, and third sections of the pressure vessel until the failure of the sample. In some cases, changing pressure conditions comprises increasing pressure conditions in the second section of the interior cavity (e.g., by pumping water or other fluid into the second section of the interior cavity through a central port extending from an outer surface of the pressure vessel to the second section of the interior cavity of the pressure vessel). In some cases, changing pressure conditions comprises increasing pressure conditions in the first and third sections of the interior cavity of the pressure vessel (e.g., by pumping water or other fluid into the first and third sections of the interior cavity through a first port extending from an outer surface of the pressure vessel into the first section the interior cavity of the pressure vessel and through a third port extending from an outer surface of the pressure vessel to the third section of the interior cavity of the pressure vessel). Failure of the sample can be indicated, for example, by a rapid change in LVDT readings, by a large increase in water or fluid needed to maintain pressure in a section of the pressure vessel, and/or by water or other fluid being expelled from another section of the pressure vessel.

Based at least in part on pressure conditions in at least one of the first, second, and third sections of the pressure vessel, one or more mechanical properties of the sample can be determined (operation 522).

The tensile strength of a sample can be determined (e.g., precisely determined or estimated) by applying increasing levels of fluid pressure to a central portion of a cylindrical sample while the end of portions of the cylindrical sample remain in a baseline pressure (e.g., atmospheric pressure or pressure consistent with downhole conditions). The fluid pressure at failure may be equal or proportional to the tensile strength of the sample. During such testing, the sample's change in length can be measured (e.g., using LVDTs) to provide a basis for calculating Young's modulus using standard methods.

A sample can also be tested under compression. For example, pressures can be increased in the first and third sections of a three-section testing apparatus until failure of the sample cement specimen. To perform compression testing, the testing apparatus can be configured with sufficient space between the initial exterior surface of the sample and the interior walls of the pressure vessel to allow for the sample being tested to expand laterally due to Poission's ratio effect.

The following example is intended to illustrate the benefits of the concepts described herein, but does not exemplify the full scope of the concepts. Thus, this example does not limit the claims.

Figure 6:
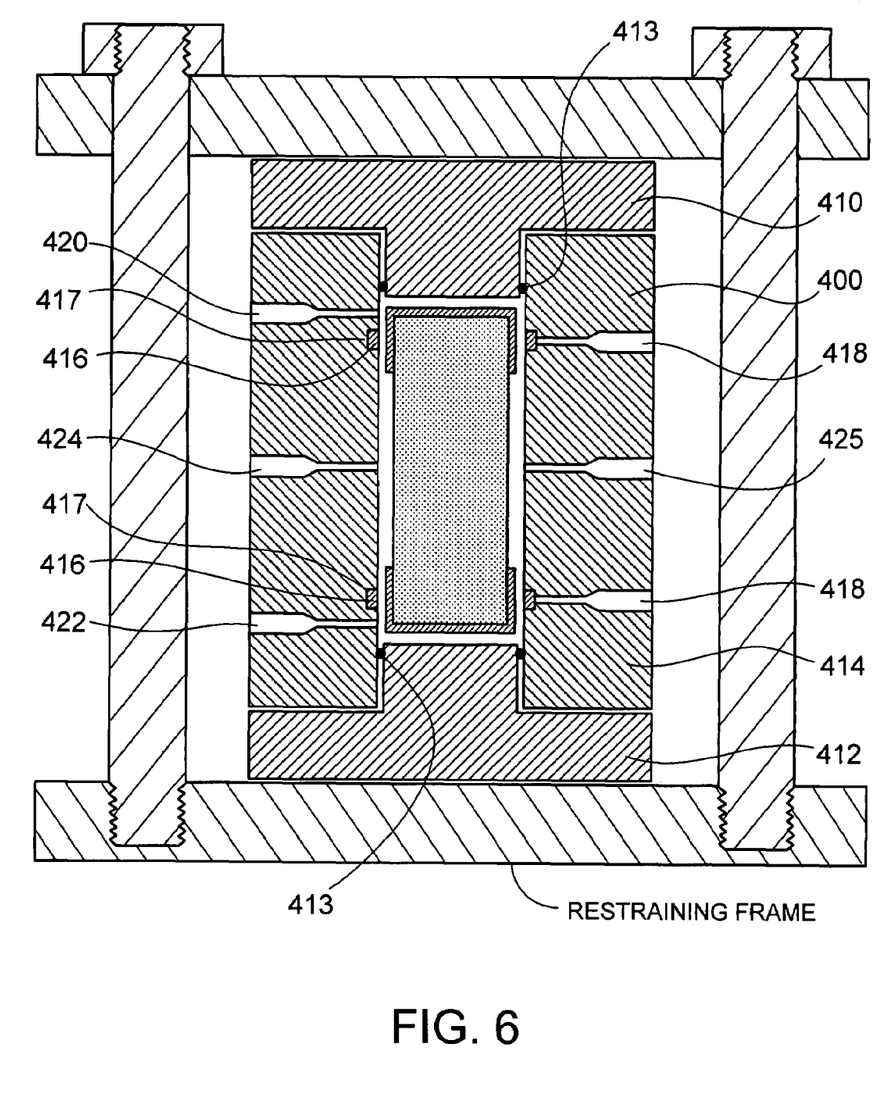
FIG. 6 is a cross-sectional view of an embodiment of a test cell.

Referring to FIG. 6, a tension cell assembly was used as the pressure test cell 400. Pressure test cell 400 included a top 410, a bottom 412, and a cylinder 414. Grooves 416 (approximately 0.207 inch wide and 0.207 inch deep) were cut into the interior surface of the cylinder 414 approximately 0.8 inch from each end of the pressure test cell 400. Rubber rings 417 (approximately 0.21 inch wide, 1 inch inner diameter, 0.21 inch thick) were installed in the grooves 416 to complete the active seal. An eighth inch national pipe thread (NPT) port 418 extended through the cylinder 414 of the pressure test cell 400 into each groove 416 to permit the seal to be pressurized. Four additional ports 420, 422, 424, 425 extended through the wall of the pressure test cell—one port 420, 422 at each end and ports 424 and 425 between the active seals. End caps comprising top 410 and bottom 412 are provided with any suitable seal 413 capable of effecting a pressure seal at the top and bottom of the cell. In this example, the seals on top 410 and bottom 412 are rubber o-rings 413 set in a groove approximately 0.25 inch from the end of the caps.

A core sample is prepared from castlegate sandstone having a diameter of about 1 inch and a length of about 2 inches. Each end of the sample is coated with a fast setting epoxy which is allowed to cure. The sample then was installed in the pressure test cell 400 with the rubber rings 417 partially supporting the sample. The end caps 410 and 412 then were place into position and the cell was placed into a restraining frame and the pressure sources were connected to the ports.

A cell manifold (not shown) included conduits connected to the top and bottom ports 420, 422. An active seal/annulus manifold included conduits connected to both active seal ports 418 and another line was attached to the ports 424 and 425 between the active seals. Interconnect piping (not shown) joining the two manifolds included an isolation valve enabling isolation of the manifolds from each other and various pressure gauges were installed in the lines. A first syringe pump was connected to the cell end manifold and a second syringe pump was connected to the active seal/annulus manifold.

After purging air from the system with water, the pressure was increased to a pressure estimated to be above the tensile strength of the sample by setting the first syringe pump to maintain a constant pressure with the isolation valve open.

The sample was allowed to equilibrate pressure at ambient temperature. After pressure equilibrium was achieved, the isolation valve was closed before the second syringe pump was brought on line and opened to the active seal/annulus manifold. The second syringe pump was then set to provide a constant water flow rate about 50 psi over the system pressure to set the seals against the core sample. The pressure applied to the ends of the sample then is slowly ramped down until the sample fails as demonstrated by a sudden drop in pressure of the middle section between the active seals. Upon removing the sample from the apparatus, the core sample was found to have a clean transverse break between the upper and lower sealed ends of the core sample. The measured and collected pressure data from one or more samples then can be used to determine the tensile failure pressure. The castlegate core sample exhibited an average tensile strength of about 22 psi.

A number of embodiments of the have been described. Nevertheless, it will be understood that various modifications may be made. For example, the illustrated testing apparatus includes two seals which divide the interior cavity of the pressure vessel into three discrete sections. Some embodiments include more seals (e.g., three seals) which divide the interior cavity of the pressure vessel into more discrete sections(e.g., four sections). Accordingly, other embodiments are within the scope of the following claims.

What is claimed is:

1. A method comprising:
    sealing a first end of a sample against passage of fluid through an end surface of the first end and through a side surface of the sample adjacent the end surface of the first end, and sealing a second end of the sample against passage of fluid through an end surface of the second end and through a side surface of the sample adjacent the end surface of the second end, while leaving a central portion of the sample between the first end and the second end substantially free of sealant;
    applying a first pressure condition to a first portion of the sample;
    applying a second pressure condition to the second portion of the sample, the second pressure condition being different than the first pressure condition; and
    determining one or more mechanical properties of the sample based at least in part on a response of the sample to the pressure conditions.

2. The method of claim 1, comprising applying either the first pressure condition or the second pressure condition to both the first and second portions of the sample.

3. The method of claim 1, wherein the first portion of the sample includes the central portion of the sample that is substantially free of the sealant.

4. The method of claim 3, wherein applying the first pressure condition comprises increasing the first pressure condition until the sample fails.

5. The method of claim 3 wherein applying the second pressure condition comprises increasing the second pressure condition until the sample fails.

6. The method of claim 3, wherein applying the first pressure condition comprises decreasing the first pressure condition until the sample fails.

7. The method of claim 3, wherein applying the second pressure condition comprises decreasing the second pressure condition until the sample fails.

8. The method of claim 1, comprising measuring elongation of the sample while applying the first and second pressure conditions.

9. The method of claim 1, wherein the first pressure condition and the second pressure condition are different than ambient conditions.

10. A method comprising:
    coating a first end and an opposite second end of a sample of porous material with a sealant while leaving a central portion of the sample between the first end and the second end substantially free of the sealant;
    applying a fluid to the sample of the porous material for at least a period of time required for the fluid applied to surfaces of the sample of a porous material to equilibrate pressure across the sample;
    applying a first pressure condition that is different from ambient conditions to a first portion of the cylindrical sample:
    applying a second pressure condition that is different from ambient conditions to a second portion of the cylindrical sample, the second pressure condition being different than the first pressure condition; and
    determining one or more mechanical properties of the cylindrical sample based at least in part on a response of the sample to the pressure conditions.

11. The method of claim 10, comprising activating an active seal to isolate a first pressure zone from a second pressure zone.

12. The method of claim 10, wherein applying the first pressure condition comprises increasing the first pressure condition until the sample fails.

13. The method of claim 10, wherein applying the second pressure condition comprises increasing the second pressure condition until the sample fails.

14. The method of claim 10, wherein applying the first pressure condition comprises decreasing the first pressure condition until the sample fails.

15. The method of claim 10, wherein applying the second pressure condition comprises decreasing the second pressure condition until the sample fails.

16. The method of claim 10, comprising measuring elongation of the sample while applying the first and second pressure conditions.

17. The method of claim 10, comprising attaching a linear variable displacement transducer to the sample with a first surface of the linear variable displacement transducer oriented towards the sample and a second surface of the linear variable displacement transducer oriented away from the sample and providing a hydraulic connection between a first pressure zone acting on the first surface of the linear variable displacement transducer and a second pressure zone acting on the second surface of the linear variable displacement transducer.

18. A method comprising:
    coating a first end and an opposite second end of a sample of porous material with a sealant while leaving a central portion of the sample between the first end and the second end substantially free of the sealant;
    isolating an upper and a lower section of a sample material from a middle section of the sample material;
    applying a first pressure condition to the upper and lower sections of the sample;
    applying a second pressure condition to the middle section of the sample; and changing the first pressure condition or the second pressure condition to another pressure condition and determining one or more mechanical properties of the sample based at least in part on a response of the sample to the change in pressure conditions.

19. The method of claim 18 comprising activating active seals to isolate the upper and lower section from the middle section of the sample.

20. The method of claim 18, wherein applying the first pressure condition comprises increasing the first pressure condition until the sample fails.

21. The method of claim 18, wherein applying the second pressure condition comprises increasing the second pressure condition until the sample fails.

22. The method of claim 18, wherein applying the first pressure condition comprises decreasing the first pressure condition until the sample fails.

23. The method of claim 18, wherein applying the second pressure condition comprises decreasing the second pressure condition until the sample fails.

24. The method of claim 10 wherein coating the first end and the opposite second end of a sample of porous material with a sealant comprises coating the first end and the opposite second end of the sample of porous material with a resin sealant.

25. The method of claim 11 wherein activating the active seal comprises engaging a portion of the sealant with the active seal.

26. The method of claim 18 wherein coating the first end and the opposite second end of a sample of porous material with a sealant comprises coating the first end and the opposite second end of the sample of porous material with a resin sealant.

27. The method of claim 19 wherein activating the active seals to isolate the upper and lower section from the middle section of the sample comprises engaging a portion of the resin sealant on the first and second ends with the active seals.

* * * * *